United States Patent
Erickson (10) Patent No.: US 9,289,546 B2
(45) Date of Patent: Mar. 22, 2016

(54) EXSANGUINATION PREVENTING DEVICE

(71) Applicant: Dirk Jerome Erickson, Seattle, WA (US)

(72) Inventor: Dirk Jerome Erickson, Seattle, WA (US)

(*) Notice: Subject to any disclaimer, the term of this patent is extended or adjusted under 35 U.S.C. 154(b) by 352 days.

(21) Appl. No.: 13/967,512

(22) Filed: Aug. 15, 2013

(65) Prior Publication Data

US 2014/0234166 A1  Aug. 21, 2014

Related U.S. Application Data

(60) Provisional application No. 61/684,040, filed on Aug. 16, 2012.

(51) Int. Cl.
*A61M 1/36* (2006.01)
*A61M 1/00* (2006.01)
*A61M 1/16* (2006.01)

(52) U.S. Cl.
CPC ............ *A61M 1/3653* (2013.01); *A61M 1/0007* (2014.02); *A61M 1/0021* (2013.01); *A61M 1/168* (2013.01); *A61M 1/1629* (2014.02); *A61M 1/3627* (2013.01); *A61M 2205/364* (2013.01)

(58) Field of Classification Search
CPC ............ A61M 1/0007; A61M 1/0021; A61M 1/1629; A61M 1/168; A61M 1/3653; A61M 2205/364
See application file for complete search history.

(56) References Cited

U.S. PATENT DOCUMENTS

| | | | |
|---|---|---|---|
| 3,965,896 A | 6/1976 | Swank et al. | |
| 4,424,053 A | 1/1984 | Kurtz | |
| 4,898,572 A | 2/1990 | Surugue nee Lasnier | |
| 5,002,529 A | 3/1991 | Cunningham | |
| 5,055,198 A | 10/1991 | Shettigar et al. | |
| 5,078,677 A | 1/1992 | Gentelia et al. | |
| 5,101,804 A * | 4/1992 | Cohn ....................... | 126/263.01 |

(Continued)

FOREIGN PATENT DOCUMENTS

| | | |
|---|---|---|
| DE | 102004033425 | 1/2006 |
| EP | 0573117 | 12/1993 |

(Continued)

OTHER PUBLICATIONS

Kolomyejtsyev_WO_2012_008872 A1—English Machine Translation.*

(Continued)

*Primary Examiner* — Tatyana Zalukaeva
*Assistant Examiner* — Benjamin Klein
(74) *Attorney, Agent, or Firm* — Themis Law (57) ABSTRACT

In one embodiment, an exsanguination preventing device includes a collection container having an inlet configured to receive blood from a patient and an outlet configured to discharge the blood; a pump operatively coupled to the collection container; a conduit fluidly coupled to the collection container, which receives the blood from the collection container, the blood being moved by the pump; and an insertion device, which delivers the blood from the conduit to a bodily part of the patient. The collection container is configured to be sealingly coupled to a wound on the patient and air entrapped within the exsanguination preventing device is removed by an air removal system, such to prevent unwanted discharge of air into the bodily part of the patient. All the components of the exsanguination preventing device are sized such to make it portable in a pocket of a garment or backpack of a soldier.

19 Claims, 6 Drawing Sheets

(56) References Cited

U.S. PATENT DOCUMENTS

| | | | |
|---|---|---|---|
| 5,275,585 A | 1/1994 | Olson et al. | |
| 5,279,550 A | 1/1994 | Habib et al. | |
| 5,387,204 A * | 2/1995 | Olsson et al. | 604/317 |
| 5,411,472 A | 5/1995 | Steg et al. | |
| 5,634,893 A | 6/1997 | Rishton | |
| 5,643,193 A | 7/1997 | Papillon | |
| 5,658,271 A * | 8/1997 | Loubser | 604/410 |
| 5,707,357 A | 1/1998 | Mikhail et al. | |
| 5,876,611 A * | 3/1999 | Shettigar | 210/739 |
| 6,017,493 A * | 1/2000 | Cambron et al. | 422/44 |
| 6,231,560 B1 | 5/2001 | Bui et al. | |
| 6,315,751 B1 * | 11/2001 | Cosgrove et al. | 604/5.01 |
| 6,342,071 B1 * | 1/2002 | Pless | 623/3.1 |
| 6,548,241 B1 * | 4/2003 | McBurney et al. | 435/2 |
| 6,613,035 B1 | 9/2003 | Longo et al. | |
| 6,776,303 B2 | 8/2004 | Fripps | |
| 6,951,553 B2 | 10/2005 | Bubb et al. | |
| 7,569,742 B2 | 8/2009 | Haggstrom et al. | |
| 2001/0029956 A1 | 10/2001 | Argenta et al. | |
| 2002/0120240 A1 | 8/2002 | Bagga | |
| 2005/0274672 A1 * | 12/2005 | Tu et al. | 210/645 |
| 2006/0222533 A1 * | 10/2006 | Reeves et al. | 417/420 |
| 2008/0091174 A1 | 4/2008 | Alam et al. | |
| 2009/0081079 A1 | 3/2009 | Johns | |
| 2009/0093754 A1 | 4/2009 | Hartig et al. | |
| 2009/0275884 A1 | 11/2009 | McNulty et al. | |
| 2011/0015590 A1 | 1/2011 | Svedman et al. | |
| 2011/0106047 A1 * | 5/2011 | Burbank et al. | 604/500 |
| 2012/0157942 A1 | 6/2012 | Weston et al. | |
| 2014/0066281 A1 * | 3/2014 | Weasler et al. | 494/34 |

FOREIGN PATENT DOCUMENTS

| | | |
|---|---|---|
| EP | 0728491 | 8/1996 |
| EP | 2389966 | 11/2011 |
| SU | 1410993 | 7/1988 |
| WO | 9113677 | 9/1991 |
| WO | 9408640 | 4/1994 |
| WO | 9817340 | 4/1998 |
| WO | 03002425 | 1/2003 |
| WO | 2012000681 | 1/2012 |
| WO | 2012008872 | 1/2012 |
| WO | WO 2012008872 A1 * | 1/2012 |
| WO | 2012034569 | 3/2012 |

OTHER PUBLICATIONS

Written Opinion of the International Searching Authority.

* cited by examiner

EXSANGUINATION PREVENTING DEVICE

FIELD OF THE INVENTION

The present invention relates to a device that prevents exsanguination. More particularly, the present invention relates to a device that prevents exsanguination of a patient by recirculating autologous blood into the body of the patient.

BACKGROUND OF THE INVENTION

Exsanguination (colloquially known as bleeding out) is the fatal process of blood loss to an amount that causes death.

A typical cause of exsanguinations is traumatic injury where blood loss cannot be arrested. For example, exsanguination is the leading cause of death on a battlefield. Non-battlefield causes can include murder by shooting or stabbing; motor vehicle accidents; suicide by cutting arteries; and partial or complete amputation of limbs due to workplace accidents.

A victim does not have to lose all of his (her) blood to cause death. Depending upon the age, health, and fitness level of the individual, a victim may die from losing half or two-thirds of their blood. In battlefield situations, blood loss of an injured soldier may not be arrested to a sufficient degree during combat or in field hospitals, and blood loss to a fatal amount may occur during transport to a care center.

Auto-transfusion systems are known in the art, as evidenced, for example, by U.S. Pat. No. 6,951,553 to Bubb et al.; US 2009/0093754 to Hartig et al.; U.S. Pat. No. 5,078,677 to Gentelia et al.; U.S. Pat. No. 5,634,893 to Rishton; and U.S. Pat. No. 5,055,198 to Shettigar et al. Those systems, however, are bulky and not particularly suited for use in a battlefield, or in other emergency situations such as a fire rescue or an accident in a remote location where trained personnel or hospital equipment may not be readily available.

In those situations, application to the patient of a system in the prior art may be difficult; and air or dirt may become trapped within the system and be lethal to the patient; or blood recirculation may be defective, exposing the patient to the risk of oxygen deprivation and permanent damage.

SUMMARY OF THE INVENTION

The present invention prevents exsanguination by use of a blood recirculating system that keeps a victim alive, for example, when an arterial laceration occurs. In one embodiment, particularly suited for military applications, an exsanguination preventing device according to the invention is simple to use and of a size that allows high portability, such that it can be carried by a potential user (for example, a soldier) together with other supplies in a pocket of a garment (which includes a pocket attached to a belt), or of a backpack, or within similar equipment. That system is suited for use by operators of different skill levels, for example, by a medic, a fellow soldier that has received adequate training, or the victim himself.

By using an exsanguination preventing device according to the invention, loss of blood is slowed or completely stopped by closing the circuit opened by the injury, which otherwise would cause an excessive loss of blood. With such a device, the life of the patient is saved by allowing him to survive until he is delivered to an operating room.

One embodiment of the invention includes the use of different attachments and power system, by which an exsanguination preventing device according to the invention can be maintained operational with different power sources while continuing to operate effectively, for example, by switching seamlessly from battery power to power provided by a power source in an ambulance or transport helicopter.

In its most basic configuration, an exsanguination preventing device according to the invention includes a collection system, which has an inlet configured to receive blood from a patient and an outlet configured to discharge the blood; a pump, which is operatively coupled to the collection system; a conduit, which is fluidly coupled to the collection system and receives the blood from the collection system through the pump; and an insertion device, which delivers the autologous blood from the conduit to a bodily part of the patient.

In one embodiment, the collection system includes a collection container, which is configured to be sealingly coupled to a wound on the patient and has an air removal system, such to prevent unwanted discharge of air into the bodily part of the patient. In alternative embodiments, the air removal system (or a supplemental air removal system) is provided at the pump or in the conduit.

In one embodiment, the inlet of the collection container is attached to the wound by one or more adhesive edges that are sealingly attached to a periphery of the wound; or by an elastic band that tightly encircles a protruding portion of the patient's body having the wound; or by a support band that extends from the inlet and tightly wraps around a part of the patient's body, such as the neck or the torso, in order to maintain the inlet in stable position about the wound.

In one embodiment, the collection container has a decanter shape with a narrower portion in the proximity of the inlet, which gradually expands to form a wider base where the collected blood is stored. This configuration facilitates a positioning of the collection container on a surface, for example on the ground during field use. Further, the base of the collection container may have a larger weight than the upper portion, to ensure that the blood collects where the outlet of the collection container is situated.

The wall of the collection container may be coated or otherwise exposed to a blood anti-coagulant to prevent coagulation of the blood stored in the collection container. Further, the air removal system may be coupled to an antimicrobial filter.

In different embodiments, the collection container may include one or multiple filters that prevent the flow-through of particles having a size above a predetermined level, and may be made of a material or have attachments suited to receive a substance injected therein. For example, the collection container may have a needle inlet, a self-sealing port, a self-sealing surface, or an attachment point for a donor bag.

In one embodiment, the inlet of the collection container and the body of the collection container, and the body and the collection container and the pump, are removably coupled to one another, so that the body of the collection container can be attached or detached, enabling a medic or other attending person to select a container inlet or body of appropriate size and shape according to need, or anyway to change the collection container for any reason, for example, in the event of a leak or contamination.

In one embodiment, the collection system includes a hollow probe configured to be inserted into the patient and receive the blood from a wound inside the patient, for example, a wound to the heart. The hollow probe may include an expanding device such as a balloon, which is provided on an outer portion of the hollow probe, that is, on all or a part of the outer surface of the hollow probe.

Such expanding device may include a stabilizing member which may be a portion of the expanding member. In that embodiment, the stabilizing member may be shaped as a balloon with an hourglass shape, the narrow portion of which is positioned against the perimeter of the thorax of the patient, locking the hollow probe into position. In another embodiment, the stabilizing member may be threaded device, which can move the hollow probe longitudinally after insertion into the wound opening.

The hollow probe may feed the collected blood to an I.V. tube for delivery to the pump, or may be fluidly coupled to a collection container, which in turn delivers the blood to the pump.

The pump of an exsanguination preventing device according to the invention may be peristaltic, and may be powered from a single source such as a battery, or may be powered alternatively by a battery or by another external power source such as an electrical outlet of a rescue vehicle or a field hospital, a solar panel, or a mechanical crank, and seamless transitions from one power system to the other, possibly with the support of a capacitor.

The recirculating pump is configured to be operated at a plurality of flow rates, and may be operatively coupled to a capacitor providing for a rapid increase in flow rates or to maintain power in an event of failure of a primary power source.

In one embodiment, a control unit is coupled to one or different sensors that provide predetermined information extracted from the blood flowing through the pump. A data port may also be provided to transmit that predetermined information to a remote location.

In one embodiment, a heating and/or cooling system heats and/or cools the blood flowing through the pump or through the delivery conduit. The heating or cooling action may be achieved by mixing two chemical products, which react and generate an exothermic or endothermic reaction.

A cannula, catheter, needle or intraosseous device is coupled to an end of the conduit to deliver the recirculated blood to the patient.

In one embodiment, the exsanguination preventing device includes a sterilizing device, which sterilizes the blood before or during flow through the conduit, for example by exposing the blood to an ultraviolet light and a sterilizing product provided in the collection container and/or the conduit.

An oxygenating device may also be included that provides oxygen to the blood. One such oxygenating system is based on pumping blood through hollow plastic fibers perforated with holes so tiny that only gas molecules can pass through them. As blood filters through the fibers, carbon dioxide escapes through the holes and is replaced by oxygen in the air or provided to the system. Preferably, such an oxygenation device is spliced inline within the delivery conduit, for example, using quick connect/disconnect fittings as joining points along the delivery conduit to allow for quick installation and removal.

BRIEF DESCRIPTION OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

DETAILED DESCRIPTION OF EMBODIMENTS OF THE INVENTION

Detailed descriptions of embodiments of the invention follow. It is to be understood, however, that the present invention may be embodied in various forms. Therefore, the specific details disclosed in the present description are not to be interpreted as limiting, but rather as a representative basis for teaching one skilled in the art how to employ the present invention in different systems or manners.

In its most basic configuration, an exsanguination preventing device according to the invention includes three major components: a collection system receiving blood from a patient; a pump, moving the blood; and a conduit, receiving the blood from the pump and delivering the whole, autologous blood back to the patient through an insertion device. Various interchangeable attachments may also be provided. All components are sized such to make the exsanguination preventing device portable in a pocket of a garment or of a backpack of a soldier.

Figure 1:
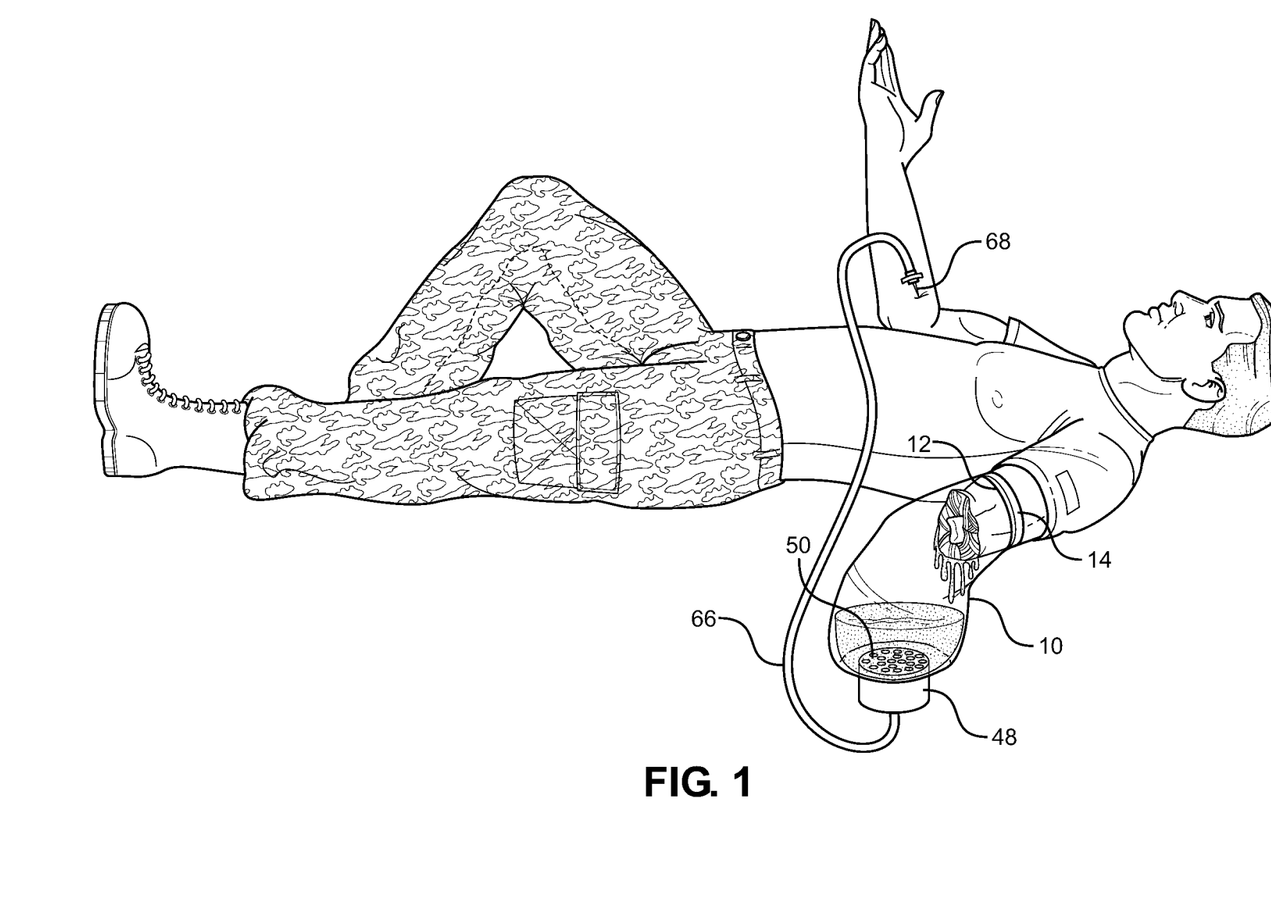
FIG. 1 illustrates an exsanguination preventing device according to the invention applied to an arm injury.

The first major component is a collection system, which in a first embodiment of the invention is a collection container or reservoir 10 that captures most or all blood escaping through the wound of a patient, for example, through the outer exposed opening of a truncated limb of a soldier in a battlefield as shown in FIG. 1.

In a preferred embodiment, collection container 10 is made of a soft, collapsible and medical grade material. In other embodiments, collection container 10 is made of a rigid medical grade material and may be used, for example, when an attending clinician prefers to avoid a squeezing of collection container 10, which may affect the flow of blood from the patient to the pump, or to use a collection container that has greater stability when positioned on the ground or other support structure.

Collection container 10 has an inlet 12 with one or more edges 14 that are configured to form a seal around the wound and capture blood flow. In one embodiment, the edges can have one or more adhesive borders that attach to the body of the victim and possibly to themselves or other parts of the reservoir if necessary to create a proper seal when inlet 12 is too large to fit snugly around an exposed limb or other wound.

Figure 2:
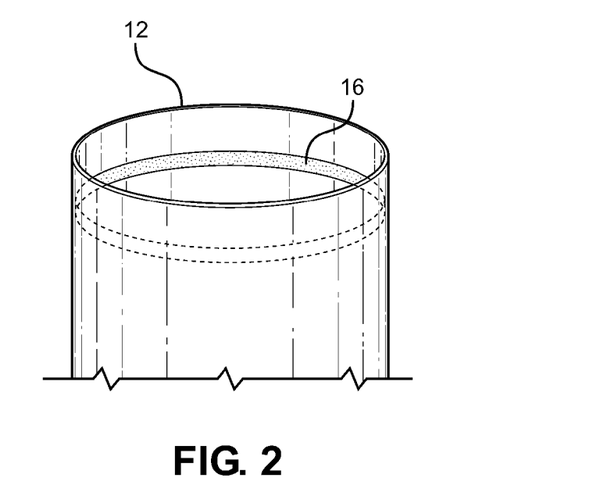
FIG. 2 illustrates an adhesive coupling applied to the collection container of the device of FIG. 1.
Figure 3:
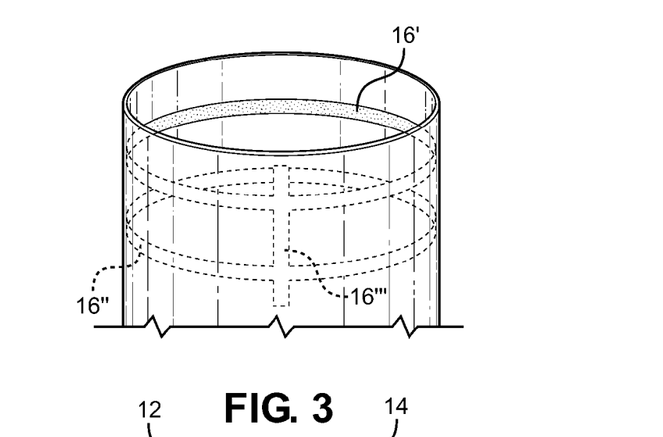
FIG. 3 illustrates an alternative adhesive coupling.

In the embodiment illustrated in FIG. 2, edge 14 is shaped as an adhesive circular band 16 disposed all around the inner wall of inlet 12. In other embodiments, a plurality of adhesive bands may be provided along edge 14, which may be parallel to one another, and/or disposed cross-wise from one another, as shown by reference numbers 16', 16" and 16''' in FIG. 3.

Figure 4:
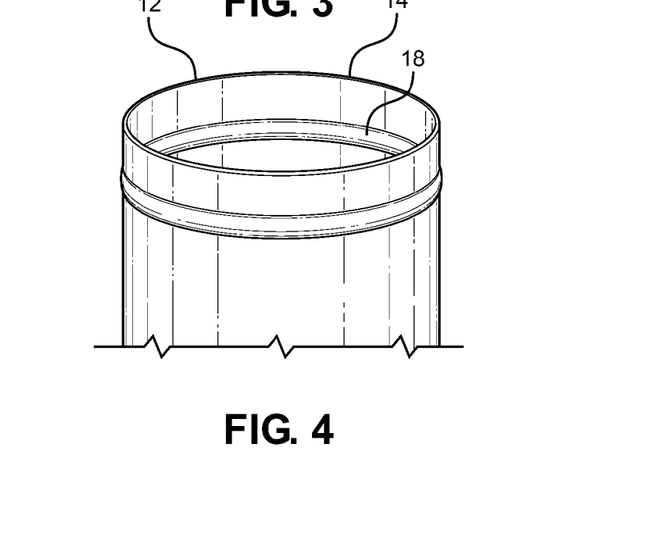
FIG. 4 is a detail view of a collection container with an alternative coupling system.

In still other embodiments, other means of attachment of inlet 12 may be used in addition to or in alternative to adhesive bands 16. For example, an elastic band 18 may be provided within edge 14 to create a seal or at least provide a stable coupling between collection container 10 and the body of the patient.

More generally, collection container 10 may be provided with inlets of different size and different modes of attachment to the body of the patient, making it suitable for use with wounds or amputations of different sizes. In the embodiment illustrated in FIG. 1, the mode of attachment to the body is provided by a collar-type adhesive band, which is particularly suited for inlets wrapped around protruding parts.

Figures 5, 6, 7:
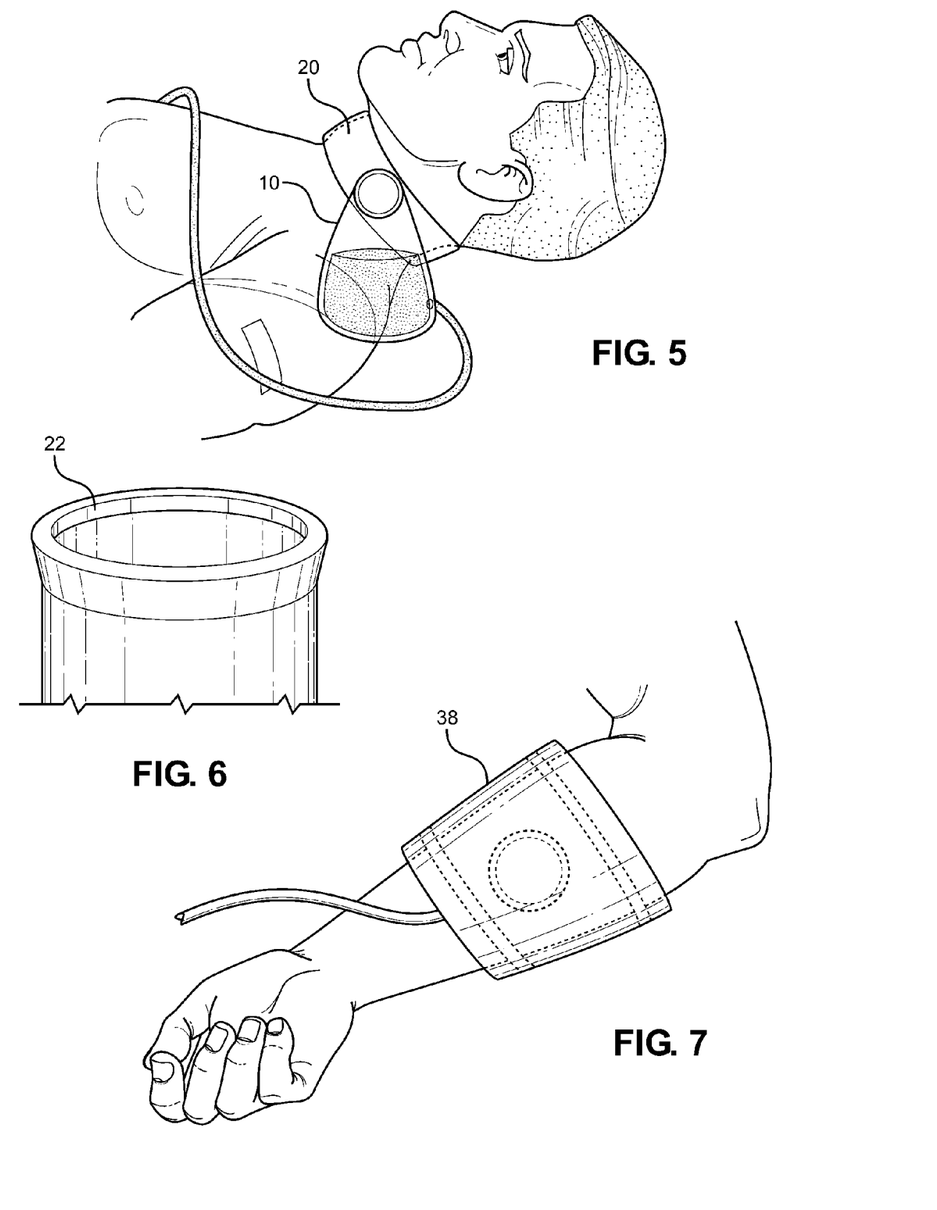
FIG. 5 illustrates still another alternative coupling system.
FIG. 6 illustrates yet another alternative coupling system.
FIG. 7 illustrates an alternative shape of the collection container.

Other embodiments of the invention include still different types of inlets and attachment modes. As an example, FIG. 5 shows an embodiment having a band 20 that can be wrapped around the neck of the patient or other body part, for example, around the torso or a limb to maintain inlet 12 in stable position. Band 20 can be fastened onto itself with Velcro (hook-and-loop), a buckle, or other coupling system known in the art. As another example, FIG. 6 shows an extended flange-shaped collar 22 that can be disposed and attached around a specific wound, for example, a bullet wound. Flange-shaped collar 22 may be coupled to a collection container having an inlet shaped as the front portion of a trumpet, which has a wide front opening coupled to a narrower neck. As a further example, FIG. 7 shows a collection container 10 that is shaped as a sleeve 38 having adhesive and/or elastic ends that can be slid over and engage a limb of the patient, creating a seal both above and below the wound.

The body of collection container 10 may also have different shapes. As mentioned previously, collection container 10 may be a soft bag that can be easily rolled up and packed together with other field supplies. Alternatively, collection container 10 may have a variety of other shapes, for example, a canteen shape, a cylindrical shape, or an ogival (bullet) shape, with rigid or flexible walls.

Figures 8, 9, 10:
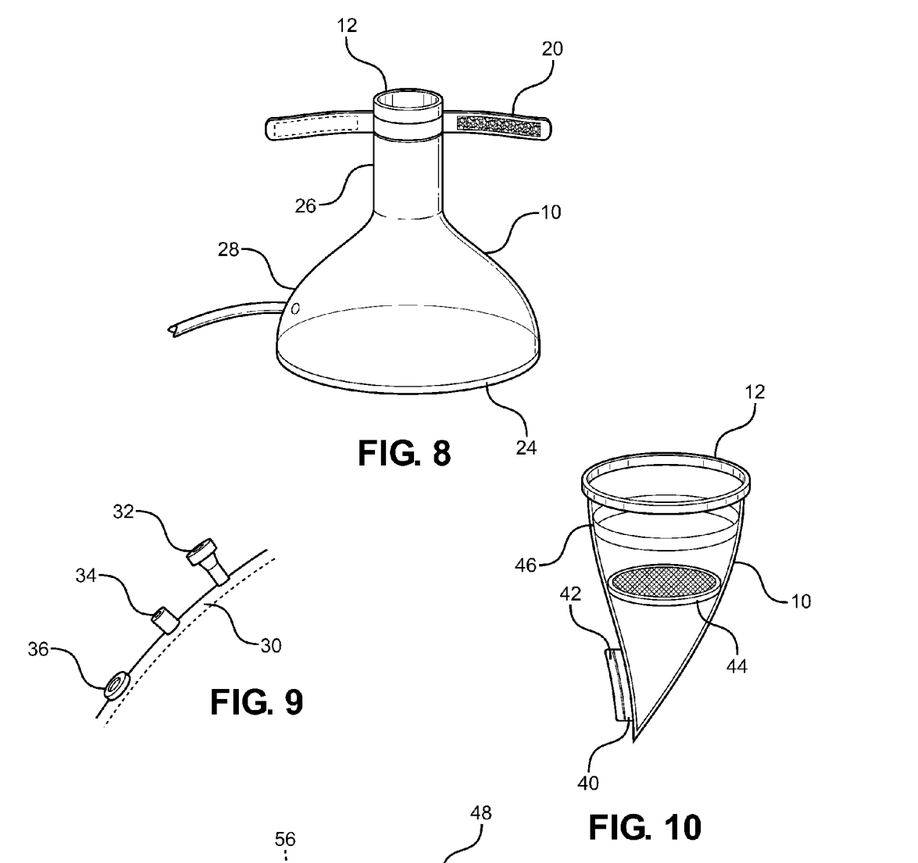
FIG. 8 illustrates a collection container having a weighted bottom according to one embodiment of the invention.
FIG. 9 illustrates a detail view of a collection container having an anti-coagulant coating and a quick-connect fitting, a self-sealing port or wall and a dedicated attachment point.
FIG. 10 illustrates a collection container having an air vent with an air filter and a particle filter.

In one embodiment, shown in FIG. 8, collection container 19 is weighted, that is, it has a heavier bottom surface 24 produced, for example, by embedding a weight therein. Such weighted bottom increases the weight of the lower portion of collection container 10 and enables an attending medic to keep collection container 10 in a desired position, for example, by laying bottom surface 24 against the ground. Further, such weighted bottom ensures that the blood collects where the container outlet is, so that there is a continuous flow of blood to the pump. Additionally, weighted bottom surface 24 provides a grabbing point to carry collection container 10 when the patient is moved to a different location.

FIG. 8 also shows another possible shape of collection container 10. In this embodiment, collection container has a narrower neck 26 in the proximity of inlet 12, which progressively widens to form an expanded base 28, giving collection container 10 a shape reminiscent of a wine decanter. With this configuration, collection container 19 can be laid flat below the wound and collect blood without having to elevate the patient.

In still another embodiment, shown in FIG. 10, collection container 10 is wider near inlet 12 and tapers down narrowing in the direction of its outlet. This shape provides for a wider collection area of the blood near the inlet and directs the blood in the direction of the outlet.

Because collection container 10 is configured to receive blood, which is then recirculated into the patient, an anticoagulant substance may be provided to which the collected blood is exposed. With reference to FIG. 9, an anticoagulant substance 30 such as citrate is coated on walls 32 of collection container 10 or is provided with other means used in the art, for example, for the blood bags of blood banks. The anticoagulant substance is preferably provided in time-released form, which is of great importance when the exsanguination preventing device must be operational for an extended amount of time, for example, when the arrival of a rescue helicopter is delayed or it is otherwise impractical to move the patient, for example, when a group of soldiers is under attack.

As further shown in FIG. 9, collection container 10 may include a quick-connect fitting 34 for an intravenous (I.V.) line, or otherwise be provided with a self-sealing port 32 or a self-sealing wall, to enable insertion of a needle or other device that delivers a desired substance to the blood. Further, collection container 10 may be configured to receive blood from a donor bag either through a dedicated attachment point 36, or through the above described quick-connect fitting 34, or through injection into self-sealing port 32 or the self-sealing wall.

With reference now to FIG. 10, collection container 10 has an air vent 40 that prevents air from being trapped in the collection container during application to the wound site, and allows 100% of collection container 10 to be filled with blood instead of blood and air. Further, removal of air is necessary to avoid embolism in the patient. The air vent preferably includes an anti-microbial filter 42 to prevent pathogens from entering the sterile bag after it is applied to the wound and sealed in place. In other embodiments, air vent 40 and anti-microbial filter 42 are provided elsewhere in the system, either as separate or joined components, for example, at pump 48 and/or conduit 66.

In one embodiment, collection container 10 (or conduit 66) also has a particle filter 44 (for example, a mesh-type screen) that is suspended across the width of collection container 10 to collect sediments and prevent the sediments from reaching the patient. Particle filter 44 removes all sediments larger than a predetermined size and prevents them from entering the pump, preventing a clogging of the pump, and as importantly prevents those sediments from reaching the vasculature of the patient. Such sediments may be present especially with blast-related wounds and may include shrapnel, bone chips and sediment form the explosion. One or more additional filters may be positioned in the proximity of outlet 50 of collection container 10.

While the preceding description relates to an exsanguination preventing device having a single collection container 10 fixedly attached to an inlet 12, in different embodiments, collection container 10 may have a body that is removably attached to inlet 12 and/or to pump 48, in order to enable the attending medic to use a collection container having an inlet and/or body of proper shape and size according to need. Such a removable attachment may be achieved, for example, with mutually coupling adhesive bands 46 (FIG. 10), with a threaded or bayonet attachment, or with other attachment systems known in the art.

Further, a system according to the invention may include a plurality of collection containers, each of which may be collect blood from a different injury if the patient suffers from multiple injuries.

The second major component of an exsanguination preventing device according to the invention is pump 48, which is operatively coupled to outlet 50 of collection container 10 and which may be either manually operated or be capable of automatic operation as soon as a liquid such as blood is introduced. In different embodiments, either a single pump or multiple pumps may be employed. Further, pump 48 may be directly connected to outlet 50 of collection container 10, or be fluidly coupled thereto with a conduit disposed therebetween.

The troop carried variant of the invention may have a pump that is small, lightweight, compact, and battery powered, but other variants for use in medevac helicopters, ambulances and field hospitals may be larger in size and have pumps that are more powerful and that are powered by an external electrical system as found, for example, in a transport's electrical system or a hospital's power supply. Such external electrical system may include a 12V vehicle battery or 120V or 220V current.

Figure 11:
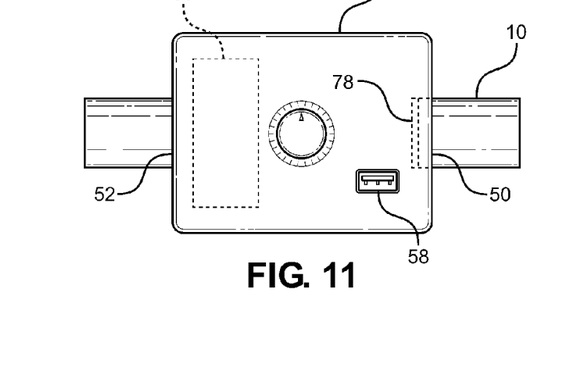
FIG. 11 illustrates a pump for an exsanguination preventing device having a battery pack and a power port.

With reference to FIG. 11, when pump 48 is battery powered, pump 48 is configured to use a battery or battery pack 56 of a type that is easily interchangeable. This allows soldiers to carry back-up batteries, always have a fully charged battery before entering into a dangerous environment, and replace the battery after prolonged use.

Backup power to pump 48 may also be provided in the form of a separate charger that is powered either by hand cranks or by solar panels. For example, a first hand crank may be employed to recharge a spent battery pack, and another one may be employed to manually operate the pump 48 when power is no longer present or pump 48 malfunctions.

Pump 48 may be coupled to the rest of the system with quick connect/disconnect fittings, so that it may be replaced with a different pump in the event of malfunction, or a second pump may be coupled to the first pump for extra power. Further, quick connect/disconnect fittings will facilitate the replacement to collection container 10 when filled, when otherwise it is desirable to replace it, or even to bypass pump 48 and connect collection container 10 directly to conduit 66.

In one embodiment, pump 48 is configured to be powered alternatively by a battery or by direct or alternating current, such that battery power may be employed in the field, and power supply may be switched to direct or alternating current when the patient is moved to a transport vehicle or a field hospital. In one embodiment, the switch from battery to 12V DC vehicle battery or 110V or 220V AC generator or hospital power is implemented by providing pump 48 with a power port 58, such that when a power cable is inserted into power port 58, the 220V AC power "takes over" in powering pump 48. A capacitor may be further provided to avoid interruptions in the power supply, or for providing a power boost when the attending medic decides to increase the flow rate of the blood.

In a preferred embodiment, pump 48 is a positive displacement pump such as a peristaltic pump, which avoids any physical contact between the blood and the inner workings of the pump, preventing contamination with exposed pump components.

Pump 48 is operated to re-introduce, back into the patient, the blood received from collection container 10, that is, the patient's own blood. The inlet of pump 48 is attached to outlet 50 of collection container 10, (either directly, or via a length of conduit), and outlet 52 of pump 48 discharges the blood into a conduit 54 that is fluidly coupled thereto, enabling the flow of the blood from collection container 10 to the patient.

In one embodiment, one or more filters are provided that remove impurities from the blood as it moves through the pump. For example, a filter may be provided near outlet 52 of pump 48.

Figure 12:
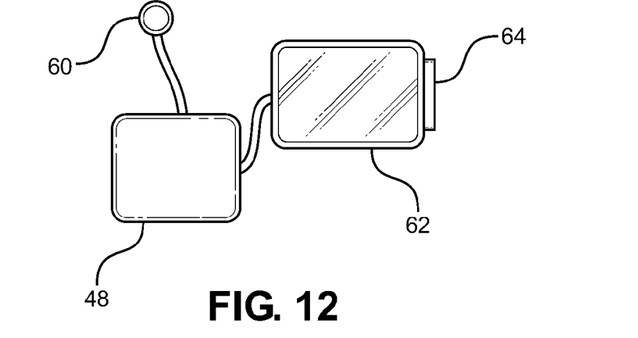
FIG. 12 is a schematic view of an embodiment of the invention having a sensor, a display and a data port.

In another embodiment, pump 48 has a sensor 78, such as an air-in-line detector, that generates an alarm signal (such as a sound or a blinking light) when air is present in the blood. Availability of such a sensor 78 is particularly important to alert a medic treating multiple casualties, or distracted by other threats, or anyway unable to remain in close proximity of the patient.

In one embodiment, pump 48 has multiple speeds for varying the flow rate of the blood. Depending on the injury, blood may need to be reintroduced into the patient's body at different flow rates. As an example, in the event of a cardiac arrest or other casualty where the heart is not pumping, blood must be artificially oxygenated and reintroduced into the patient's body at a high flow rate, for example, at a femoral artery, in order to maintain full circulation through the vascular system. As another example, a significantly slower flow rate may be required to draw blood from a donor into collection container 10 and pump it straight into the patient for a time-critical blood transfusion. With this setup, a flow-meter displaying the amount of blood passing through the pump will ensure that the donor himself does not become exsanguinated. Flow rates may be varied, for example, by rotating a knob 82 provided on an outer surface of the pump, or by depressing one of two buttons disposed next to each other on a face of pump 48.

In one embodiment, pump 48 is operatively connected to a display 62, such as a LCD display, which provides an attending medic with a read-out of vital patient information received from one or more sensors 60. Further, display 62 can provide desired information on the operation of the system, for example, pump speed.

Display 62 may be positioned on a face of pump 48 or be a separate component that is operatively coupled to pump 48. Moreover, pump 48 may be operatively connected to a data port 64 (whether or not a display 46 is available) that transmits patient information to medical personnel through a wired or wireless connection, to monitor patient conditions and prepare for the necessary treatment when the patient is delivered. A microprocessor elaborates the information received from the one or more sensors 60 and causes display 62 to put that information in readable form.

Additional information may be provided by additional attachments to the system, for example, a saturation of peripheral oxygen ($S_pO_2$) attachment placed on the patient's finger or ear. Other attachments may provide information including, without limitation, body temperature, pulse or heart rate, volume of blood pumped through the system, arterial oxygen saturation ($S_aO_2$), hemoglobin count, respiration rate, and blood pressure.

All such collected information can be shown on display 62, either simultaneously by having the medic scroll through a menu, and/or can be relayed wirelessly to en-route medics or to surgeons preparing for surgery. Such relay may be performed by connecting a satellite phone, radio, computer, or other device capable of transmission to the exsanguination preventing device through data port 64, or by coupling a system microprocessor with a transmission port.

The third major component of a device according to the invention is a conduit 66, which is coupled to pump 48 at its proximal end and to an insertion device 68 at its distal end.

Insertion device 68 may be a hypodermic needle, a cannula, or a catheter that discharges the blood from conduit 66 to a bodily part of the patient, thereby re-introducing the blood into the patient's bloodstream. Insertion devices of this kind are known in the art and, accordingly, are not described here in detail.

Conduit 66 is made of a flexible material such as a medical grade elastomer (polypropylene, nylon and dynaflex) or medical grade silicone, and operates in a manner similar to an I.V. line for intravenous therapy.

The gauge of conduit 66 and the type of insertion device 68 needed to successfully re-introduce the necessary volume of blood into the patient may vary. A conduit 66 of a single size may be used for increased portability and interoperability, or conduit 66 may be changed with one of a plurality of interchangeable conduits of different sizes according to the situation at hand.

Likewise, a device according to the invention may be provided with a plurality of insertion devices 68, from which the attending medic can select the one most suited for the situation at hand. In that event, each of insertion devices 68 is provided with a quick connect/disconnect system for a quick changeover.

In some situations, obtaining intravenous access is a prolonged process requiring more than several minutes or is altogether impossible because of hypovolemia and collapsed peripheral blood vessels. In addition, establishing central intravenous access is time-consuming and may interfere with other resuscitation activities, especially when the internal jugular or subclavian site is the potential access site. If the medic is unable to find a suitable intravenous access, an intraosseous device may be employed to re-infuse the blood directly into the bone marrow. In that event, sites of insertion may be the sternum, proximal or distal tibia and humerus.

Figure 13:
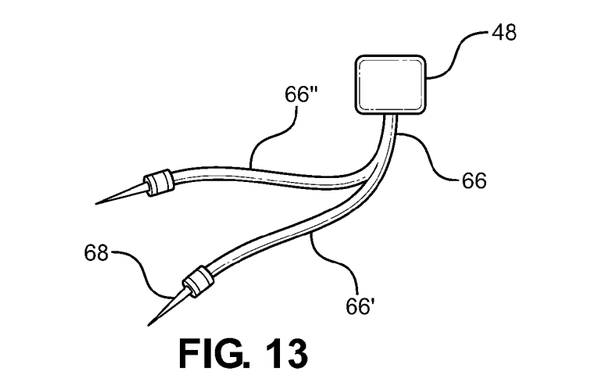
FIG. 13 illustrates a branching conduit in an exsanguination preventing device according to the invention.

In one embodiment, conduit 66 splits into a plurality of conduits (shown as 66' and 66" in FIG. 13), each with its own insertion device to be inserted into different bodily parts of the patient (for example, one in each arm). This design could overcome a single vein's inability to handle a large enough flow required to sustain life and minimize blood loss.

In one embodiment, conduit 66 has "piggyback" sites similar to those provided in a standard I.V. line, which can be used to add additional blood products, a saline solution, or a medication. Multiple bags of donor blood can also be piggybacked into collection container 10 or conduit 66. In one embodiment, conduit 66 includes one or more collection containers 10 or is coupled to one or more reservoirs along its length, in order to stabilize blood supply to the receiving bodily part.

As mentioned, conduit 66 preferably has one or more air filters that remove small air bubbles that may have entered the system and that are preferably disposed inline.

In one embodiment, a device according to the invention includes a sterilizing device, which sterilizes the blood before or during flow through conduit 66. Such sterilizing device may include a UV light, an ion filter that kills bacteria, a chemical additive, or a combination thereof.

Figure 14:
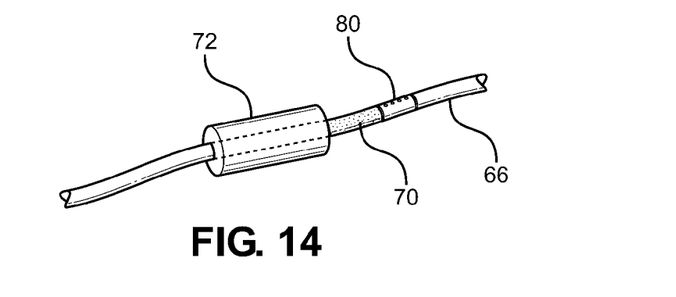
FIG. 14 illustrates a portion of a conduit having a riboflavin coating, which is exposed to UV light.

For example, a UV light may be employed in conjunction with riboflavin, a combination which has been proven to kill bacteria in blood. In one embodiment, shown in FIG. 14, this combination is provided by having a collection container 10 that is lined with, or that otherwise exposes, the blood to riboflavin 70 (as well as citrate or heparin for anticoagulation purposes), or by injecting the riboflavin into a "piggyback" site or a self-sealing point in collection container 10. The blood exposed to riboflavin 68 enters a portion of conduit 66 which is exposed to UV light 72, which activates the riboflavin, generating a reaction that has a sterilizing effect.

On sunny days, exposure to UV light provided by the sun may be sufficient. Otherwise, UV light can be provided with a chemical glow stick (sometimes called a "chem-light" stick) that encases a portion of the I.V. line and provides the necessary amount of needed UV light on the blood/riboflavin mixture passing through that section of line. In one embodiment, the UV light is produced by passing an electric current through a gas or vapor, such as mercury vapor.

Ion filters may also assist in the removal of any microbes or bacteria that may otherwise be fatal.

Figure 15:
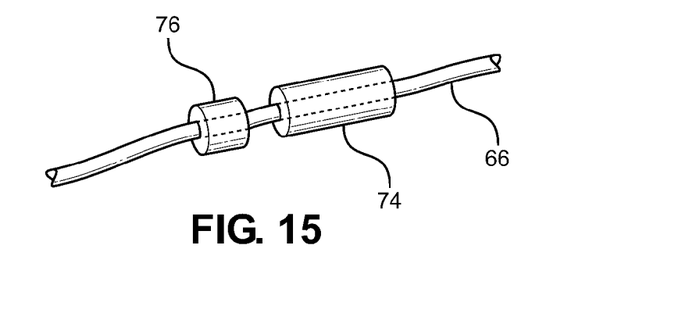
FIG. 15 illustrates a portion of conduit operatively coupled to a cooling system and to an oxygenation system.

It may be desirable to heat or cool the blood recirculated to the patient, for example, to cool the blood in situations such as neurogenic fever or therapeutic hypothermia, or to heat the blood to prevent unwanted hypothermia or to treat for shock. In one embodiment of the invention, a cooling and/or heating system is provided inside pump 48 or along a section of the conduit 66. For brevity, the following description will relate to a cooling system.

Cooling system 74 may include a "chem-light" type chemical stick that encases a section of conduit 66. Similar to a chem-light stick, cooling system 74 comprises a plastic tube that contains a glass tube with a separate chemical therein. When the glass tube is broken, the chemical combines with another substance (typically a liquid) in the plastic tube, mixing the two chemicals and creating an endothermic reaction. Likewise, heating can be provided with an exothermic reaction caused by a different combination of chemical products, as known in the art.

In one embodiment, a device according to the invention includes an oxygenating system 76. One type of oxygenating system 76 is based on pumping blood through hollow plastic fibers perforated with holes, which are so tiny that only gas molecules can pass through them. As blood filters through the fibers, carbon dioxide escapes through the holes and is replaced by oxygen provided to the system by surrounding air or by an oxygen storage unit. Oxygenating system 76 is preferably spliced into conduit 66 utilizing quick-attachment points.

A similar system is used in the BioLung being developed by Michigan Critical Care Consultants (MC3).

Adding an oxygenating system 76 is extremely important, because if the patient experiences cardiac arrest, pump 48 can force oxygenated blood into the patient at a sufficiently high enough pressure, acting as an external heart until an attending physician is able to employ a heart assisting device or other circulation-maintaining device or otherwise until the patient can be revived in the field, in an ambulance or at a hospital.

Adding an oxygenating system 76 may prove life-saving not only for injured soldiers, but also for patients that have suffered a stroke, a heart attack, or electrocution. Re-oxygenating the blood before it reaches a patient can also improve the symptoms of shock deriving from other life-threatening injuries where shock is present.

Considering that collection container 10 may be provided in collapsible form and conduit 66 is also flexible, and that a compact, portable pump may be used, the complete device may be not much larger than pump 48, making is extremely portable.

Figure 16:
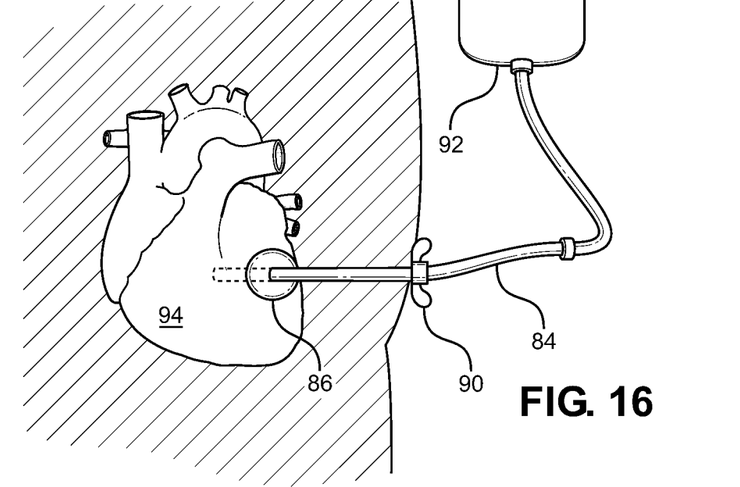
FIG. 16 illustrates an exsanguination preventing device according to the invention having a probe applied to the heart.
Figure 17:
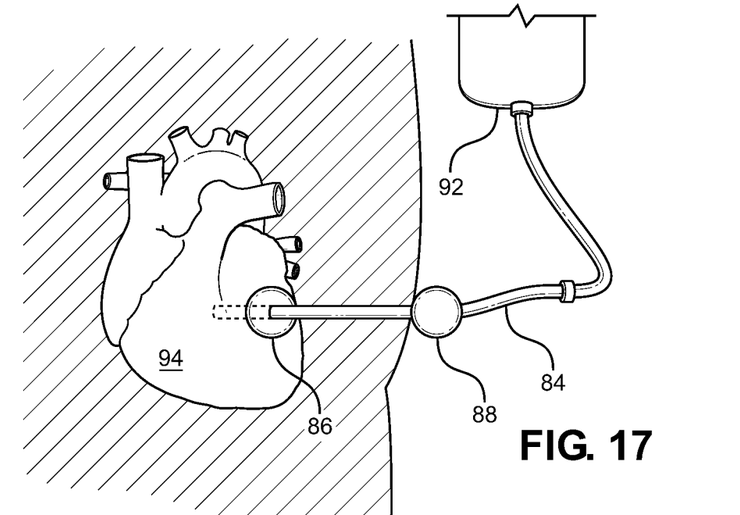
FIG. 17 illustrates another exsanguination preventing device according to the invention having a probe applied to the heart.

In different embodiments of the invention, shown in FIGS. 16 and 17, the blood collection system is provided as a hollow probe 84, which is introduced into the patient. Such probe 84 extracts blood from the body of the patient and may be shaped as a cannula, which may or may not have an inflation feature. This embodiment finds application when the wound opening, that is, the source of blood loss, is positioned deep inside the patient's body, for example, when the heart 94 has been punctured.

A probe according to the present embodiment may be utilized in lieu of or in conjunction with a collection container 92 to collect the blood. Further, multiple probes may be "piggybacked" into the same collection container 92 or meet at a "Y" junction in the tube leading to the pump. This is advantageous when the patient has multiple puncture sites or an entry and an exit wound from the same puncture.

In one variant, the probe is shaped as a large bore needle or a cannula that is inserted into the thoracic cavity to remove and re-circulate blood caused by internal bleeding.

In one variant, probe 84 is of expanding nature and has an inflatable design provided by a balloon 88, as explained in greater detail below. In another variant, the probe may have an alternative design that still expands on contact with the blood, for example, be in the form of a feminine tampon.

Regardless of the specific design, a probe collects blood "upstream" of the pump, either replacing or feeding collection container 92. One or more filters may be disposed within the probe or in a conduit transferring the blood from the site of the injury to the pump. When a collection container is also utilized, all filters built into the collection container will be utilized in lieu of or in addition to any filters provided in probe 84.

Further, the probe and/or a conduit connecting the probe to the collection container or the pump will be provided with anti-coagulation properties (for example, by coating the inner wall of the probe and/or conduit with an anticoagulant product) due to the rapid clotting observed in blood from internal bleeding.

A probe according to the present embodiment is inserted into the body of the patient (for example, into a heart puncture) and inflated using a distal balloon 86 disposed thereabout. Balloon 86 is then in proper position to plug the wound by compression in the proximal direction.

In one embodiment, balloon 86 expands to have an hourglass or "8" shape defined by a second balloon portion 88, or balloon 86 may alternatively be provided in two different sections, one of which anchors the probe against the inner wall of heart 94, and the second one of which inflates progressively from the proximal to the distal direction until it makes contact with the outer wall of the thorax. In another embodiment, a threaded member 90 (for example, a screw down portion) may be provided on the outside of probe 84 and move along probe 84 until contact is made with the thoracic wall, stabilizing probe 84 in position or even pulling probe 84 outwardly (or pushing it inwardly) and allowing balloon 86 to create a seal inside of the wound opening. A quick-connection fitting may be used to couple probe 84 to the tube, which connects probe 84 to container 92 or to the pump.

The tube which goes through the balloon can then extract blood out of the target bodily part of the patient, such as the thoracic cavity or the heart, and begin the recirculation process.

A device according to one of the embodiments of the invention can be made to have such a degree of portability that a soldier, a medic or other rescue personnel can carry such a compact, lightweight, and lifesaving device in a pouch of his flak jacket, making it easily accessible if the need arises. A soldier who receives an arterial injury can have a collection container 10 sealed around the injury within seconds, with pump 48 connected and insertion device 68 inserted into a receiving bodily part only a few seconds later.

A device according to the invention provides a soldier with the equivalent of carrying multiple gallons of blood (possibly an unlimited number) of his own blood type on his person. Otherwise, it is unfeasible to have each soldier carry a sufficient amount of his own blood type or other compatible blood type, and soldiers or medical personnel may also be unable to carry blood in the field due to lack of refrigeration. In addition, a shortage of donor blood may occur due to the combination of long-distance voyage to the battlefield, brief shelf-life of the blood, and scarcity of donors. Moreover, older blood may have undergone a loss of oxygen transport capacity, so an exsanguination preventing device according to the invention provides a patient with the best option for blood transfusion when required, because the patient's own blood is used, which is fresh, not subject to rejection, and free from transmittable diseases.

Proper availability and use of an exsanguination preventing device according to the invention undeniably improves the chance of survival every time and will save countless lives, making it a must-have item for every soldier deployed in combat.

A device according to the invention also finds useful applications in non-combat situations, for example, for people who live or work in remote locations or perform hazardous occupations such as police officers or firefighters.

While the invention has been described in connection with the above described embodiments, it is not intended to limit the scope of the invention to the particular forms set forth, but on the contrary, it is intended to cover such alternatives, modifications, and equivalents as may be included within the scope of the invention. Moreover, the scope of the present invention fully encompasses other embodiments that may become obvious to those skilled in the art.

The invention claimed is:

1. An exsanguination preventing device comprising:
a collection system having an inlet configured to receive blood from a patient and an outlet configured to discharge the blood;
a pump operatively coupled to the collection system;
a conduit fluidly coupled to the collection system, the conduit receiving the blood from the collection system, the blood being moved from the collection system to and through the conduit by the pump; and
an insertion device configured to discharge the blood from the conduit to a bodily part of the patient,
wherein the inlet of the collection system is configured to sealingly couple the inlet to a wound on the patient,
wherein the exsanguination preventing device comprises an air removal system, such to prevent unwanted discharge of air into the bodily part of the patient,
wherein the collection system comprises a collection container,
wherein the inlet of the collection container is configured to be sealingly coupled to the wound by having one or more of: adhesive edges sealingly attaching to a periphery of the wound, a band configured to tightly encircle a protruding portion of the patient's body with the wound therein, or a support band extending from the inlet and configured to tightly wrap around part of the patient's body such to maintain the inlet in stable position about the wound, and
wherein the inlet is removably coupled to a body of the collection container, such that a support person is enabled to couple different inlets to different bodies of collection containers, thereby selecting a combination of the inlet and the body according to need.

2. The exsanguination preventing device according to claim 1, wherein the collection container has a decanter shape comprising a narrower first portion in proximity of the inlet which gradually expands to form a wider base where the collected blood is stored.

3. The exsanguination preventing device according to claim 2, wherein the base of the collection container is configured to have a larger weight than the first portion of the collection container such to increase weight of the collection container when the first portion is in an upper position and the base is in a lower position.

4. The exsanguination preventing device according to claim 1, wherein the collection container is provided with a blood anti-coagulant to prevent coagulation of the blood stored in the collection container.

5. The exsanguination preventing device according to claim 1, wherein the air removal system comprises a vent having an anti-microbial filter.

6. The exsanguination preventing device according to claim 1, wherein the collection container comprises one or more filters configured to prevent flow-through of particles having a size above a predetermined level.

7. The exsanguination preventing device according to claim 1, wherein the collection container is configured to receive a substance injected therein, and wherein the substance is injected through a needle inlet, a self-sealing port or surface of the collection container, or an attachment point of a donor bag.

8. The exsanguination preventing device according to claim 1, wherein the pump is peristaltic.

9. The exsanguination preventing device according to claim 1, wherein the pump is configured to be powered alternatively from a battery or an outer source selected from the group consisting of an electrical outlet of a rescue vehicle or a field hospital, a solar panel or a mechanical crank.

10. The exsanguination preventing device according to claim 1, wherein the pump is equipped with a sensor configured to detect presence of air within the blood.

11. The exsanguination preventing device according to claim 1, wherein the pump is configured to be operated at a plurality of flow rates.

12. The exsanguination preventing device according to claim 11, further comprising a capacitor providing for a rapid increase in the flow rates or to maintain power in an event of failure of a primary power source.

13. The exsanguination preventing device according to claim 1, further comprising a control unit coupled to one or more sensors providing predetermined information calculated from the blood flowing through the exsanguination preventing device or attachments thereto.

14. The exsanguination preventing device according to claim 13, further comprising a data port configured to transmit the predetermined information.

15. The exsanguination preventing device according to claim 1, further comprising a heating or cooling system configured to heat or cool the blood flowing through the pump or through the conduit.

16. The exsanguination preventing device according to claim 15, wherein the heating or cooling system is configured to cause a heating or cooling of the blood by mixing two chemical products, which react causing an exothermic or endothermic reaction.

17. The exsanguination preventing device according to claim 1, further comprising a sterilizing device sterilizing the blood before or during flow through the conduit, the sterilizing device comprising one or more of an ultraviolet light and a sterilizing product, or an ion filter, provided in one or more of the collection container, the pump, or the conduit.

18. The exsanguination preventing device according to claim 1, further comprising an oxygenating device providing oxygen to the blood.

19. The exsanguination preventing device according to claim 18, wherein the oxygenating device is provided inline in the conduit.

\* \* \* \* \*